(12) United States Patent
Augustine

(10) Patent No.: US 6,176,870 B1
(45) Date of Patent: *Jan. 23, 2001

(54) INFLATABLE THERMAL BLANKET WITH SURGICAL ACCESS FOR USE WITH PATIENTS IN THE LITHOTOMY POSITION

(75) Inventor: Scott D. Augustine, Bloomington, MN (US)

(73) Assignee: Augustine Medical, Inc., Eden Prairie, MN (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/910,906

(22) Filed: Aug. 13, 1997

(51) Int. Cl.[7] ........................................... A61F 7/00
(52) U.S. Cl. ................................................. 607/107
(58) Field of Search .......................... 607/107, 104, 607/105, 106, 108; 165/46; 5/487, 485

(56) References Cited

U.S. PATENT DOCUMENTS

| 222,690 | 12/1879 | Goldschmidt . | |
|---|---|---|---|
| 1,399,095 | 12/1921 | Webb, Sr. . | |
| 1,777,982 | 10/1930 | Popp . | |
| 2,093,834 | 9/1937 | Gaugler | 128/145 |
| 2,110,022 | 3/1938 | Kliesrath | 5/334 |
| 2,122,964 | 7/1938 | Sweetland | 34/26 |
| 2,512,559 | 6/1950 | Williams | 5/347 |
| 2,601,189 | 6/1952 | Wales, Jr. | 4/160 |
| 2,706,988 | 4/1955 | Weber | 128/402 |
| 3,243,827 | 4/1966 | Kintner | 5/334 |
| 3,418,726 | 12/1968 | Sparks | 34/99 |
| 3,610,251 | 10/1971 | Sanderson | 128/379 |
| 3,610,323 | 10/1971 | Troyer | 165/46 |

(List continued on next page.)

FOREIGN PATENT DOCUMENTS

| 33 08 553 | 3/1983 | (DE) . |
|---|---|---|
| 0 113 420 | 11/1983 | (DE) . |
| 0 311 336 | 8/1988 | (EP) . |

(List continued on next page.)

OTHER PUBLICATIONS

Webster's Ninth New Collegiate Dictionary definition of "laminate".

Webster's Third New International Dictionary, p. 250, definition of "bond".

(List continued on next page.)

Primary Examiner—Mark S. Graham
(74) Attorney, Agent, or Firm—Gray Cary Ware Freidenrich

(57) ABSTRACT

An inflatable thermal blanket includes an inflatable covering inflated through an inlet by a thermally-controlled inflating medium. An aperture array on the undersurface of the inflatable covering exhausts the thermally controlled inflating medium from the inflatable covering. The inflatable thermal blanket is adapted for controlling a patient's body temperature, when the patient is placed in the lithotomy position. The inflatable thermal blanket allows a medical practitioner access through the inflatable thermal blanket for medical purposes, and includes an inflatable portion for covering an upper extent of the patient's body, to which are joined a pair of elongate inflatable portions that cover the patient's legs. The elongate inflatable. portions are separated by an elongate opening that allows access to the care site. Uninflatable drapes may extend from the inner edges of the elongate inflated portions to maintain the temperature control medium, proximate to the patient, and away from the care site. The inflatable thermal blanket may also be provided with attachment devices placed to aid the positioning of the blanket on the patient, and for contouring to the patient's shape in the lithotomy position. The inflatable thermal blanket allows a medical practitioner to easily access a care site while being shielded from the air flow that is generated by the blanket in order to warm the patient.

28 Claims, 11 Drawing Sheets

U.S. PATENT DOCUMENTS

| | | | |
|---|---|---|---|
| 3,691,646 | 9/1972 | Ruffolo | 34/90 |
| 3,714,947 | 2/1973 | Hardy | 128/400 |
| 3,757,366 | 9/1973 | Sacher | 5/347 |
| 4,572,188 | 2/1986 | Augustine et al. | 128/380 |
| 4,660,388 | 4/1987 | Greene, Jr. | 62/261 |
| 4,777,802 | 10/1988 | Feher | 62/3 |
| 4,807,644 | 2/1989 | Sandhaus | 128/849 |
| 4,867,230 | 9/1989 | Voss | 165/46 |
| 5,125,238 | 6/1992 | Ragan et al. | 62/259.3 |
| 5,184,612 | 2/1993 | Augustine | 128/400 |
| 5,300,100 | 4/1994 | Hickle et al. | 607/107 |
| 5,300,101 | 4/1994 | Augustine et al. | 607/107 |
| 5,300,102 | 4/1994 | Augustine et al. | 607/107 |
| 5,324,320 | 6/1994 | Augustine et al. | 607/107 |
| 5,336,250 | 8/1994 | Augustine | 607/107 |
| 5,343,579 | 9/1994 | Dickerhoff et al. | 5/421 |
| 5,350,417 | 9/1994 | Augustine | 607/104 |
| 5,360,439 | 11/1994 | Dickerhoff et al. | 607/104 |
| 5,384,924 | 1/1995 | Dickerhoff et al. | 5/421 |
| 5,405,370 | 4/1995 | Irani | 607/107 |
| 5,405,371 | 4/1995 | Augustine et al. | 607/107 |
| 5,443,488 | 8/1995 | Namenye et al. | 607/104 |
| 5,514,169 | 5/1996 | Dickerhoff et al. | 607/107 |
| 5,545,194 | 8/1996 | Augustine | 607/104 |
| 5,596,778 | 1/1997 | Suzuki et al. | 5/502 |
| 5,620,482 | 4/1997 | Augustine et al. | 607/107 |

FOREIGN PATENT DOCUMENTS

| | | |
|---|---|---|
| 716746 | 10/1954 | (GB) . |
| 1 334 935 | 3/1971 | (GB) . |
| 1 461 383 | 4/1973 | (GB) . |
| 1 532 219 | 6/1975 | (GB) . |
| 1 566 207 | 5/1977 | (GB) . |
| WO 85/03216 | 8/1985 | (WO) . |

OTHER PUBLICATIONS

McGraw–Hill Encyclopedia of Science & Technology, 7th Ed., p. 713, definition of "bonding".

"Normothermia in the OR" Augustine Medical, Inc., Oct. 1989.

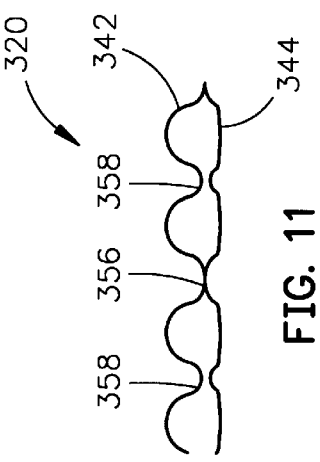
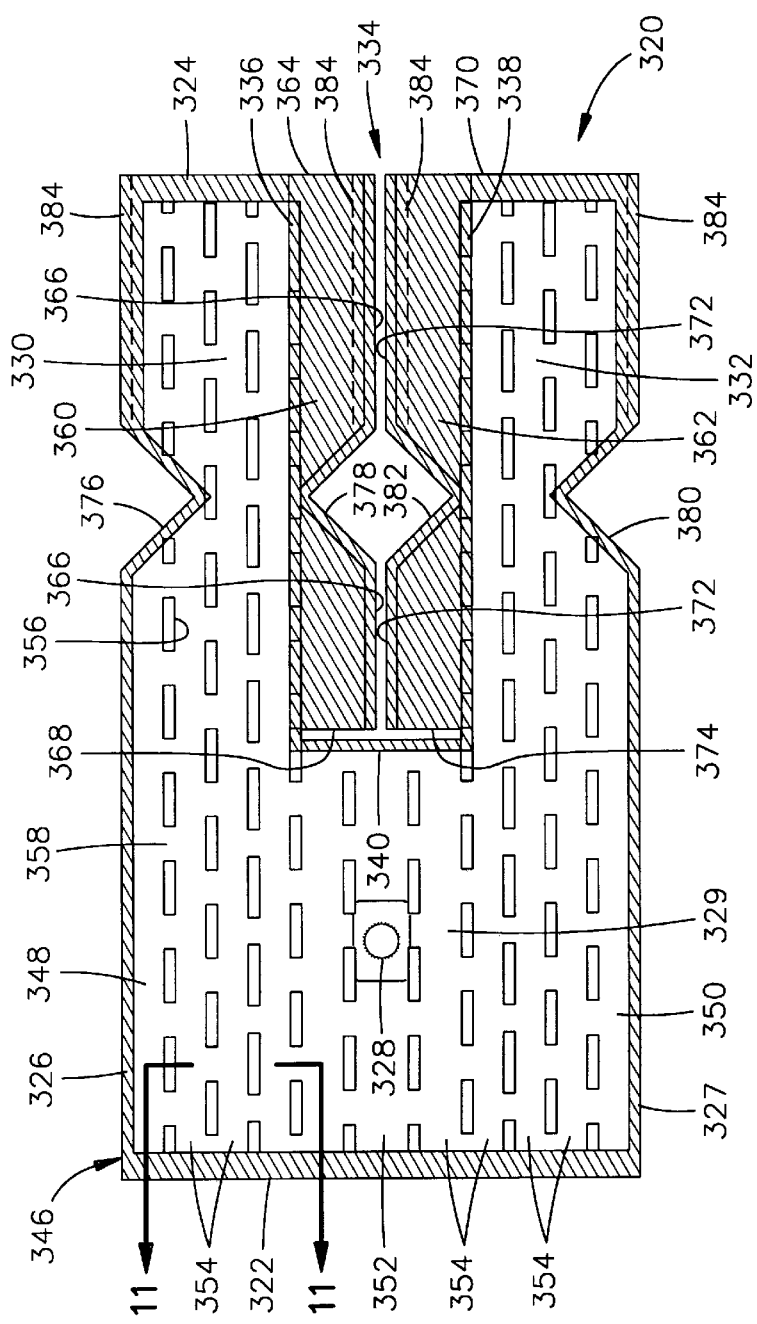

INFLATABLE THERMAL BLANKET WITH SURGICAL ACCESS FOR USE WITH PATIENTS IN THE LITHOTOMY POSITION

CROSS REFERENCE TO RELATED APPLICATIONS

This application is related to U.S. application Ser. No. 08/831,603, filed on Apr. 10, 1997, which is a continuation of U.S. application Ser. No. 08/388,730, filed on Feb. 15, 1995, which is a continuation-in-part of U.S. application Ser. No. 07,550,757, filed on Jul. 10, 1990, which is a continuation-in-part of U.S. application Ser. No. 07/227, 189, filed on Aug. 2, 1988, which is a continuation-in-part of U.S. application Ser. No. 07/104,682, filed on Oct. 5, 1987.

BACKGROUND OF THE INVENTION

1. Field of the Invention

This invention relates generally to inflatable thermal blankets used in a medical setting to deliver a bath of a thermally-controlled gaseous medium, such as warmed air, to a patient in order to control the patient's body temperature. More particularly, the invention pertains to inflatable thermal blankets to control patient body temperature during a medical procedure while providing access through the inflated blanket for medical personnel. Still more particularly, the invention is directed to inflatable thermal blankets for use with patients receiving medical care in the lithotomy position.

2. Description of the Related Art

The inflatable thermal blanket prior art is best expressed in prior U.S. Pat. No. 4,572,188 entitled "AIRFLOW COVER FOR CONTROLLING BODY TEMPERATURE," and prior U.S. Pat. No. 5,405,371 entitled "THERMAL BLANKET". In these patents, an inflatable airflow cover (i.e., inflatable thermal blanket) is inflated by the introduction into the cover of a thermally-controlled inflating medium, such as warmed air. Holes on the underside of the inflatable thermal blanket exhaust the thermally-controlled inflating medium from inside the blanket when the blanket is placed over a patient and inflated, thereby creating an ambient environment about the patient, the thermal characteristics of which are determined by the temperature of the inflating medium. These holes open through the lower blanket surface into the blanket. The inflatable thermal blanket is intended, among other things, for the treatment of hypothermia, as might occur operatively or postoperatively.

Evaluation of inflatable thermal blankets by skilled practitioners has resulted in general approbation: the opinion is that the inflatable thermal blanket efficiently and effectively accomplishes its purpose of giving a thermally-controlled bath, and is highly effective in treating hypothermic patients. However, while the prior art inflatable thermal blanket achieves its objectives, certain improvements to it are necessary in order to realize additional clinical objectives and to enjoy further advantages in its use.

For example, one use for an inflatable thermal blanket is patient temperature control during a medical procedure, such as surgery. The patient's temperature is controlled by distributing the temperature controlled air over the patient's body. But the typical inflatable thermal blanket covers the patient's entire body and it is not possible to simultaneously access the patient, for medical purposes, while the blanket lays upon the patient and is providing temperature regulation.

The difficulty in providing patient access through an inflatable thermal blanket utilizing super atmospheric temperature controlled air is that the openings formed in the blanket necessary to provide patient access permit the temperature regulated air to escape, and such access interferes with the thermal regulation desired to be achieved by the blanket. Contamination of the procedure site because of the escaping air is also a concern.

In some medical procedures, a patient is placed in a lithotomy position. In the lithotomy position, the patient is laying on his or her back while the patient's legs are bent at the knees and extend beyond the end of the operating table. The legs are supported by "stirrups" which provide support at the knees and feet. The lithotomy position is commonly used for procedures or surgery involving the genitals or rectum, such as, for example, vaginal delivery, vaginal hysterectomy, cystoscopy (viewing the bladder with a scope), TURP—transurethral resection of the prostate, hemorrhoid and rectal surgery, nephrolithotomy (kidney stone removal) and ureteral stint placement. In the lithotomy position, the doctor is positioned between the patient's legs, having convenient access to the patient's perineal region, genitals and rectum.

Patients lose a great amount of body heat in the lithotomy position because their legs are suspended in the air and are minimally insulated. Further, some of the procedures done in this position, e.g., TURP, require the use of large volumes of irrigating fluids which also cool the patient. Moreover, many patients needing prostate surgery are older, and are therefore quite susceptible to hypothermia. It is well known in the inflatable thermal blanket art that the efficiency of heat transfer to the patient is proportional to the amount of body surface area covered by the blanket or warm air bath.

Accordingly, a need exits for an inflatable thermal blanket which is capable of delivering a temperature controlled airflow to a patient in order to maintain the patient's body temperature at a desired level while simultaneously allowing access to the patient during a medical procedure. A particular need exists for an inflatable thermal blanket that can be used with patients undergoing medical procedures while in the lithotomy position. What is required is a blanket which allows unimpaired medical access to a patient in the lithotomy position, without jeopardizing the patient's health or comfort as a result of inability to effectively control the patient's body temperature.

SUMMARY OF THE INVENTION

The invention is an inflatable thermal blanket for controlling a patient's temperature, while the patient is in the lithotomy position. The inflatable thermal blanket is formed as an inflatable covering with top and bottom surfaces, and having apertures that pass through the bottom surface to allow air within the inflatable covering to flow out of the covering. An air inlet is placed in the blanket, preferably toward an end closest to the head of the patient. The end of the inflatable thermal blanket that covers and warms the legs of the patient has two elongate inflatable portions. These elongate inflatable portions of the blanket define an elongate recess having a longitudinal dimension extending between the elongate inflatable portions which allows a care giver to have convenient access to the patient's perineal region, genitals and rectum. A pair of uninflatable drape sections may be provided on the inner sides of the elongate inflatable portions to maintain the temperature controlled medium proximate to the legs and lower body of the patient and away from the care site. A pair of uninflatable drape sections may be provided on the end of the blanket closest to the head of the patient to retain the temperature controlled medium near the neck and upper body of the patient.

In a related aspect of the invention, alcoves may be provided along the edges of the elongate inflatable portions and the uninflatable drapes to allow the inflatable thermal blanket to be more easily shaped to the contour of the underside of the patient's legs, when the patient is placed in the lithotomy position. Ideally, the alcoves are wedge shaped. Attachment devices positioned on the elongate inflatable portions and the uninflatable drape sections allow the blanket to be semi-permanently secured in a contoured position to the patient's legs.

In a further related aspect of the invention, the recess may have a transverse dimension at one end of the elongate inflatable portions of the blanket to facilitate maximum surgical access, and to allow for the blanket to be temporarily sealed to the patient by an attachment device, in order to prevent the temperature controlled medium flowing from the blanket into the perineal region, or onto a medical practitioner, during a medical procedure.

In a still further aspect of the invention, a bottom surface of the inflatable thermal blanket is an undersheet of flexible fibrous material, woven or non-woven, that is bonded to a sheet of non-fibrous material, such as plastic. The fibrous material of the undersheet provides greater comfort to the patient because it comes into contact with the patient's skin.

In the operation of preferred embodiments of the invention, a heater/blower that includes a compressor and a heater supplies heated air, under pressure, to an inlet opening in the blanket. The heated pressurized air is distributed throughout the inflatable chambers and flows to the patient through the apertures in the base sheet of the inflatable thermal blanket.

Therefore the invention accomplishes the important objective of providing an inflatable thermal blanket that permits a relatively unobstructed view of, and access to, a care site when in use.

Another objective is the efficient and uniform heating of a patient when the blanket is inflated with a heated inflating medium.

A further objective is providing a covering for a patient's legs and/or feet that helps retain the heat inflating medium around the patient.

A still further objective is the provision of such a blanket with a device for maintaining the cleanliness of the care site.

A still further objective is to provide the ability to select inflatable thermal blankets adapted for specific partial areas of the patient, leaving other areas exposed for care and treatment.

A still further objective is to provide an inflatable patient temperature control blanket for use in the lithotomy position which allows surgical access through the blanket to the perineal, rectum and genital areas without negatively affecting the blanket inflation.

A still further objective is to provide an inflatable temperature control blanket allowing surgical access, wherein the blanket is capable of maintaining the desired lithotomy access opening configuration.

A still further objective is to provide an inflatable thermal blanket utilizing super-atmospheric, temperature-controlled air, wherein the blanket includes attachment devices which may be selectively employed to attach the blanket to the patient's body for maintaining positioning thereon, and to maintain the shape of the blanket to the contours of the patient's body.

The invention may thus be employed to provide numerous features which work together to allow surgical access to a lithotomy patient while allowing the patient's temperature to be regulated. The invention also minimizes the risk that escaping air might contaminate the surgical site. The advantageous simplified structure of the inflatable thermal blanket make its production straight forward and economical.

BRIEF DESCRIPTION OF THE DRAWING

These and other important objectives and advantages will become evident when the detailed description of the preferred embodiments of the invention is read with reference to the below-summarized drawings, in which:

FIG. 10 is a plan view showing an inflatable thermal blanket constructed in accordance with the present invention for use with patients in the lithotomy position, with the blanket laying flat before being inflated or placed on a patient;

FIG. 11 is a cross sectional view taken along line A—A in FIG. 10;

DETAILED DESCRIPTION OF THE PREFERRED EMBODIMENTS

Figure 1:
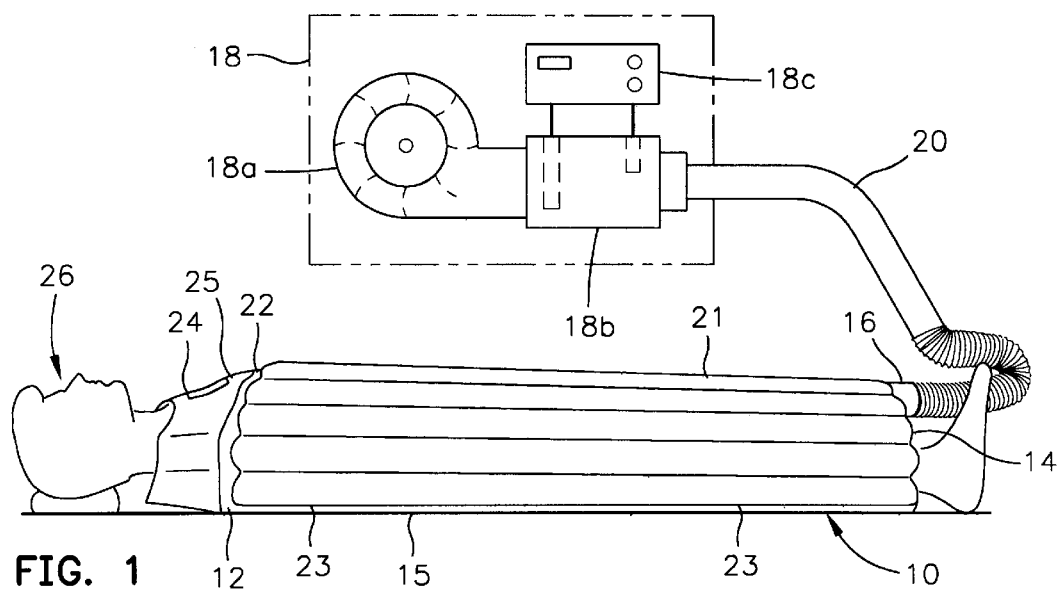
FIG. 1 is a side elevation view of an inflatable thermal blanket, in use, with associated thermal apparatus indicated schematically.

This invention is described in preferred embodiments in the following description with reference to the Drawing Figures, in which like numbers represent the same or similar elements. While this invention is described in terms of the best mode for achieving the invention's objectives, it will be appreciated by those skilled in the art that variations may be accomplished in view of the teachings herein without deviating from the spirit or scope of the invention.

Inflatable Thermal Blankets

An inflatable thermal blanket 10 illustrated in FIG. 1 has a head end 12, a foot end 14 and two lateral edges, one indicated by 15. An inflation inlet cuff 16 is connected to a heater/blower assembly 18 having a compressor 18a, a heater 18b and a control unit 18c which may include user-selectable fan speeds, controllable heat amounts and temperature control. The heater/blower assembly 18 provides a stream of heated air through a connecting hose 20. When the heater/blower assembly 18 is operated, the stream of heated air flows through the inflation cuff 16. As described below, a pattern of apertures on the undersurface of the blanket (not shown in FIG. 1) convectively delivers the inflating heated air into the interior space enclosed by the inflated thermal blanket.

The contour of the inflatable portion of the inflatable thermal blanket 10 is varied at the head end 12 of the blanket to provide an uninflated blanket recess 22 in the quilted upper surface 21, which remains smooth and flat when the blanket is inflated. Circulation of the heating air may be accelerated through the inflatable thermal blanket by exhaust port openings in the upper surface, adjacent the lateral edges of the blanket. Two exhaust ports openings are indicated by reference numeral 23. Further, a bib 24 made of an absorbent material is attached to the head end 12 of the inflatable thermal blanket in the vicinity of the uninflated recess 22. In fact, as shown in FIG. 1, the bib 24 includes a semi-circular tab 25 that extends into the recess 22.

As illustrated in FIG. 1, the inflatable thermal blanket, when placed over a person and inflated and bathes a person 26 with the thermally-controlled air used to inflate the blanket. While the patient is being thermally bathed, the uninflated recess 22 permits observation of the patient's head, face, neck, and chest from almost any location with respect to the inflatable thermal blanket 10. Thus, if the patient is placed on a gurney or a bed, the head of which is against a wall, a care giver such as a nurse, intern, resident, or doctor, can keep the patient's face under observation from the foot end 14 of the inflatable thermal blanket 10. Respiration can be detected by the rise and fall of the bib 24 and the uninflated area 22, which form an uninflatable drape that rests directly on the patient's chest. Moreover, the bib 24 will provide an absorbent sink for stray, unconfined liquids in the area of the patient's head or at the head end 12 of the inflatable thermal blanket 10.

Figure 2:
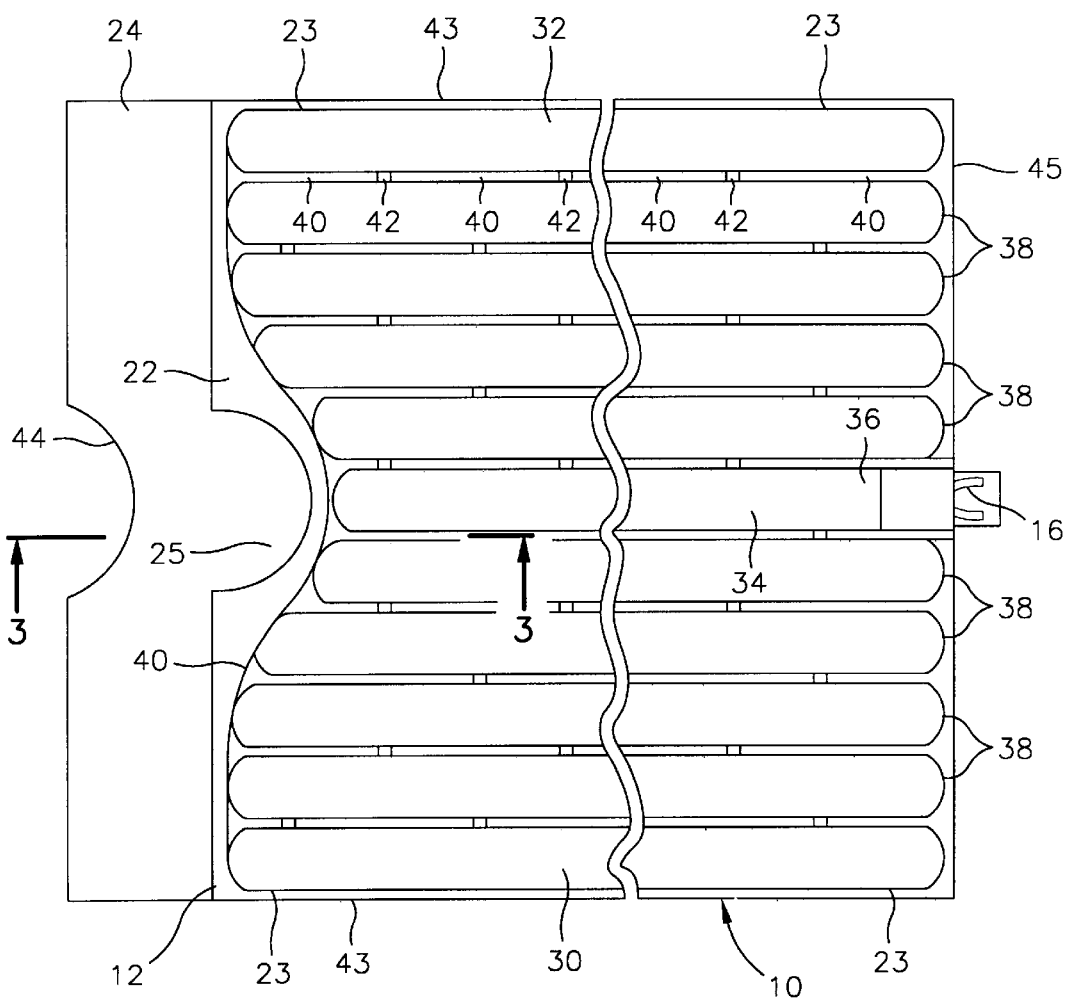
FIG. 2 is an enlarged top plan view of the inflatable thermal blanket of FIG. 1 opened flat.

FIG. 2 is a plan view of the inflatable thermal blanket 10 opened flat to illustrate one possible structure. FIG. 2 illustrates the upper surface of the inflatable thermal blanket, that is the side that is visible in FIG. 1. As seen, the upper surface consists of a parallel array of elongated tubes of which 30 and 32 are the lateral most tubes, 34 is the center tube, and the tubes 38 are arrayed between one of the lateral most tubes and the center tube. Each tube is separated from an adjacent tube by a discontinuous seam, one of which is indicated by 40. The seam 40 separates the tube 32 and its nearest adjacent neighbor 38. The discontinuous seam 40 is interrupted by passageways 42 communicating between the tubes. An interrupted seam separates every tube from one adjacent neighboring tube. The seams permit the inflatable thermal blanket, when inflated, to retain the inflating medium, while the ports 42 permit full circulation of the inflating medium throughout the array of tubes. The foot-end seam 45 is continuous. The tubes are inflated through the center tube 34, which transitions to a port 36 through which the inflation cuff 16 is inserted. The edge seams 43 are discontinuous only if the exhaust port openings 23 are needed. A seal can be made between the inflation port 36 and the inflation cuff 16 by any conventional means, for example, a cuff, an o-ring, or even tape. When the inflating medium is introduced into the center tube 34, it flows laterally from the center tube into all of the other tubes through the ports 42. Near the head end 12, a continuous seam 41 defines the forward end of all of the tubes, with the seam assuming a bell-curve shape. On the head end side of the seam 41, the inflatable thermal blanket 10 is uninflatable. The bell-shaped seam 41 thus defines the uninflated recess area 22 at the head end of the inflatable thermal blanket 10. As shown in FIG. 1, by virtue of its structural integration with the rest of the inflatable thermal blanket 10, the uninflated recess 22 forms an uninflatable drape that extends over the upper chest of the patient 26 when the blanket is inflated. This helps thermally bathe the patient while preventing the migration of air from inside the blanket 10 to the patient's head and neck area. Because the recess 22 is uninflated, it provides a wide-angled viewing gap in the inflated contour of the upper surface 21. The gap is filled by continuation of the material and base sheets of which the blanket is constructed. It is noted that the pattern of inflatable tubes can be replaced by other suitable patterns of structure. The tubes are preferred since they impart strength and shape to the bathing structure; other inflatable structures are contemplated, however.

The absorbent bib has an indent 44 cut into its outside edge, which permits the blanket to be drawn up to the chin of a patient and which provides absorbency laterally up the neck of the patient. The absorbent bib can consist of any absorbent material such as a single- or multi-ply tissue paper which is used to make paper towels.

Figure 3:
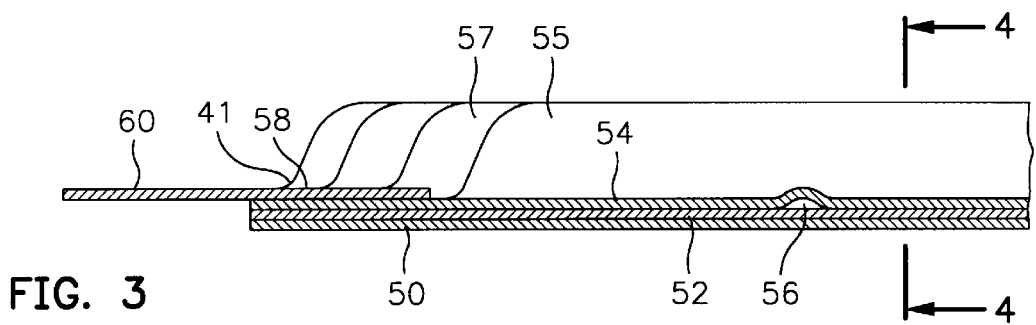
FIG. 3 is an enlarged sectional view taken along 3—3 of FIG. 2.
Figure 4:
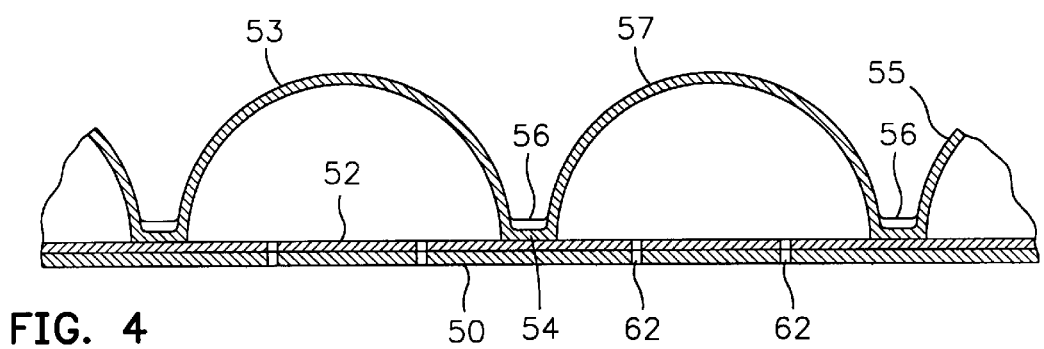
FIG. 4 is a further enlarged sectional view taken along line 4—4 of FIG. 3.

Construction details of the inflatable thermal blanket 10 are illustrated in FIGS. 3 and 4. The inflatable thermal blanket 10 is assembled from a base sheet and a top sheet. The base sheet may consist of an underside layer 50 formed from a flexible, fibrous, preferably non-woven structure composed of synthetic or natural materials capable of bonding to an upperside layer 52 of a heat-sealable synthetic material such as plastic. For example, the underside layer 50 may be a non-woven, hydroentangled polyester material and the upperside layer 52 may include a polypropylene film which is extrusion-coated on to the polyester layer 50. Alternatively, the underside layer 50 may comprise a non-woven, paper-based material to which the upperside layer 52, including either a polyethylene or polypropylene film, has been glue laminated. For example, the layers 50 and 52 may include a stratum of absorbent tissue paper prelaminated with a layer of heat-sealable plastic. Material of such construction is commercially available in production rolls and is used to make painter's drop cloths. These examples are for illustration only. Generally, the top sheet and the base sheet may be constructed using great varieties of materials and structures. In this regard, the base sheet may comprise one or more material sheets of laminar, composite, hybrid or uniform construction that exhaust or diffuse temperature-controlled air from the interior of the inflatable thermal blanket through the base sheet. The top sheet 53 of the inflatable thermal blanket preferably comprises air-impermeable materials that may be bonded to a surface of the base sheet. For example, in the case where the base sheet comprises a plastic sheet 52 the top sheet 53 may consist of a sheet of plastic bonded to the plastic upper sheet 52. In this case, the top sheet is preferably attached by a continuously running web process that includes stations which provide an interruptible heat-sealing process. This interruptible heat sealing process can be controlled to form elongate heat seals that define the inflatable tubes therebetween. The seals can be formed as continuous air impervious seals or discontinuous air permeable seals. The interruptible heat sealing process is thus used to form the continuous seams, one of which is the bell-shaped seam 41 in FIG. 2, the interrupted seams, one of which is indicated by 54, and the inflatable tubes, one of which is indicated by 55. As can be seen in FIG. 3, the interruption of the seam 54 forms a passageway 56 between adjacent tubes 55 and 57.

The absorbent bib and tab may comprise a single material layer 60/58. Alternatively, they may be formed from separate material sheets cut to the outlines illustrated in FIG. 2. The absorbent material forming the bib and tab can be bonded to the upper plastic layer by heat processing or by gluing. Preferably, the bib and tab are an uninflatable section of the base and top sheets 50 and 53, bonded together forward of the seam 41, as shown in FIG. 3.

The inventors also contemplate deletion of the bib and tab. In that instance, the inflatable thermal blanket would still have the viewing recess, which would be defined by the continuous seam at the head end, and which would be filled with the forward portion of the base sheet.

Circulation of heated air through the blanket may be enhanced by exhaust port openings 23, which open through the upper plastic sheet, which is heat sealed to the base of the blanket. The openings 23 vent the heated inflating air out of the outermost tubes 30 and 32, away from the underside of the blanket. Because air can circulate to, and through, the blanket edges, the inflating air in the outermost tubes is hotter than if the openings were absent. This results in hotter air being delivered through the underside apertures toward the edge of the blanket.

Figure 5:
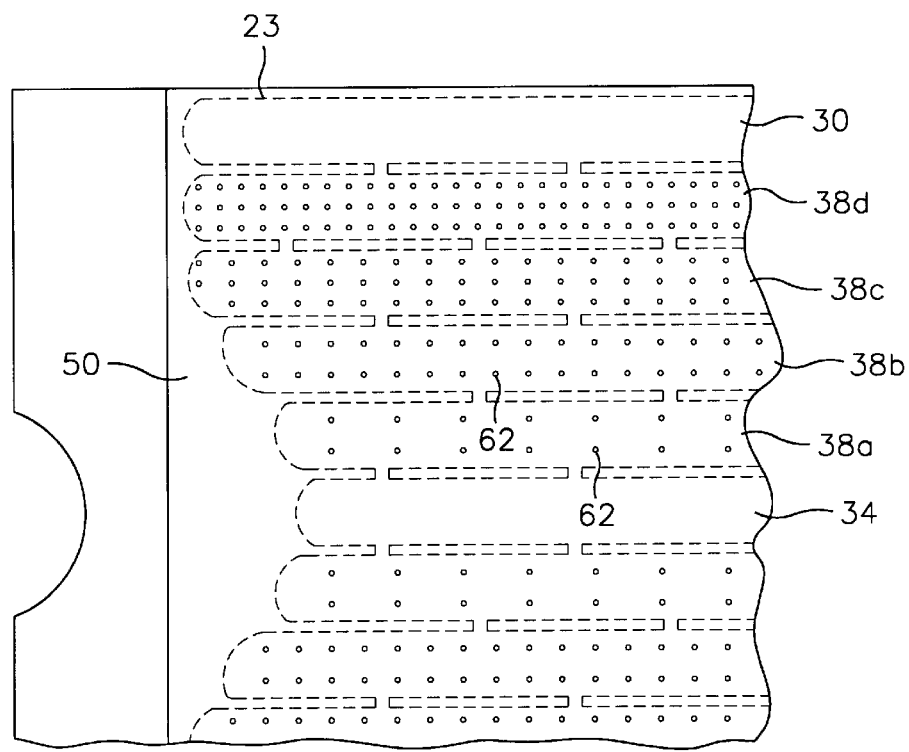
FIG. 5 is a partial underside view of the inflatable thermal blanket of FIG. 1.

The inflatable thermal blanket is enabled to bathe a patient in the thermally-controlled inflating medium introduced into the upper side tubes by means of a plurality of apertures 62 shown in FIG. 4 and 5. The apertures extend through the base sheet of the blanket, which includes the layers 50 and 52. The apertures 62 are made in the footprints of the tubes of the blanket upper side according to a pattern which has been determined to deliver a very uniform thermal bath. In this regard, no apertures are provided through the underside into the lateral most tubes 30 and 32, or into the center tube 34. In addition, the apertures 62 are provided through the underside to the apertured tubes in a density which varies inversely with the proximity of the tube to the center tube 34. Thus, the hole density increases from the tube 38*a* through the tube 38*d*. Even with the exhaust port openings, the temperature of the inflating medium exhibits a drop from the center to the lateral most tubes. The varying density of the apertures 62 tends to reduce this gradient further by forcing hotter air to the edges of the blanket. Thus, the thermal bath delivered to the patient is of a generally uniform temperature. The aperture density variation also equalizes the flow of inflating medium out of the apertures. As will be evident, the inflating pressure will be greatest at the center tube 34 and will tend to diminish toward the lateral edges of the inflatable thermal blanket. Therefore, fewer apertures are required for the tubes near the center tube 34 to deliver the same amount of air as the relatively greater number of apertures in the tubes at a greater distance from the center tube 34.

The apertures comprise openings which can be of any appropriate shape. For example, we have produced blankets with elongated apertures, approximately ¼ inch in length.

Figure 6:
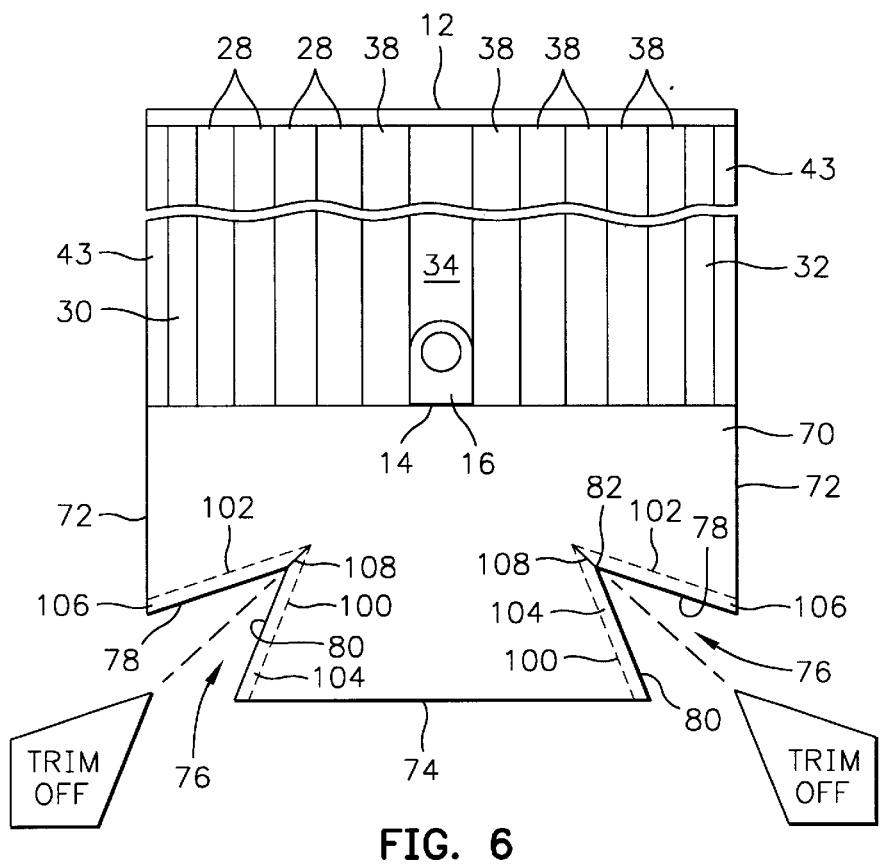
FIG. 6 is a partial diagrammatic top plan view of an inflatable thermal blanket with a partially constructed foot drape.
Figure 7:
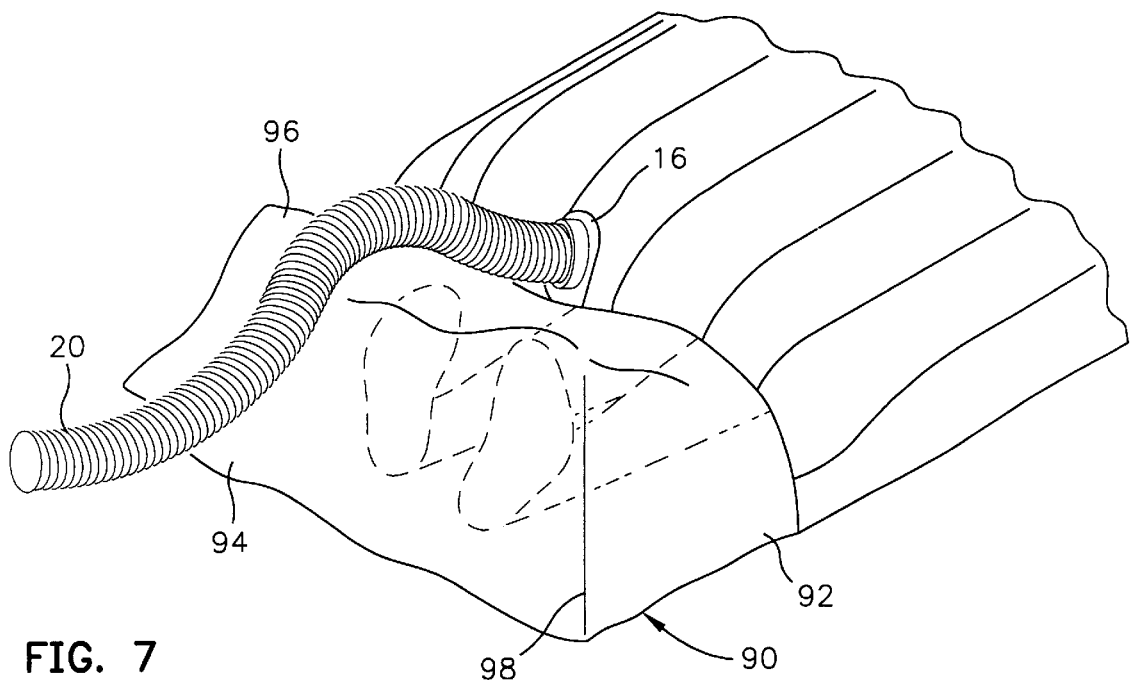
FIG. 7 is a partial projected view of the fully constructed inflatable thermal blanket of FIG. 6 in use, with the patient's feet illustrated by hidden lines underlying the foot drape.

An inflatable thermal blanket including a foot drape is shown in FIGS. 6 and 7. The foot end 14 of the inflatable thermal blanket 10 is modified to provide an uninflated drape forming section 70 formed by a rearward extension of the base sheet 50/52 and a uninflatable portion of the heat-sealable plastic top sheet bonded to the base sheet. The drape forming sheet 70 has sides 72 extending parallel to and rearwardly from the outside edge of the edge seams 43, and a rear edge 74. Optionally, the drape-forming sheet 70 further includes a pair of V-shaped cuts 76 in the rear corners thereof. The V-shaped cuts 76 are formed by converging cuts 78 and 80, extending inwardly from one of the sides 72 and the rear edge 74, respectively, to a point of intersection 82. As shown in FIG. 7, the drape-forming section 70 may be formed into an uninflatable foot drape 90 that includes a pair of side portions 92, a rear portion 94 and an upper portion 96. The drape 90 is so formed by joining the edges 78 and 80 of the V-shaped cuts 76 to form a pair of seams 98. To form the seams 98, the V-shaped cut edges 78 and 80 may be folded about respective lines 100 and 102 that parallel the edges 78 and 80, as shown in FIG. 6. The resulting respective folded surfaces 104 and 106 may then be fastened together by appropriate means such as heat sealing. Joining the surfaces 104 and 106 forms a crease 108 and transforms the two dimensional drape forming section 70 into the three dimensional drape 90.

The resultant drape 90 is uninflatable and traps and retains heat around the patient's feet to warm the feet. As shown in FIG. 7, the drape 90 also insulates the bare skin of the feet from excessive conductive heat from the inflating hose 70 in the event the hose is oriented in a position wherein it might otherwise come in contact with the feet. Patient warming and comfort is thus further enhanced.

The Invention

The invention is illustrated in multiple embodiments in FIGS. 10–19 as intended for use as an inflatable thermal blanket for patients in the lithotomy position. In the lithotomy position, illustrated in FIGS. 8 and 9, a patient 300 is reclined on an examination table 302. The patient's legs are placed into a pair of stirrups 304 which provide support at the knees 306 and the feet 308 of the patient. The stirrups 304 also create a bend in the patient's legs at the knees. A medical practitioner 310 is shown between the patient's legs accessing the patient's perineal, genital, and rectum regions.

Figure 8:
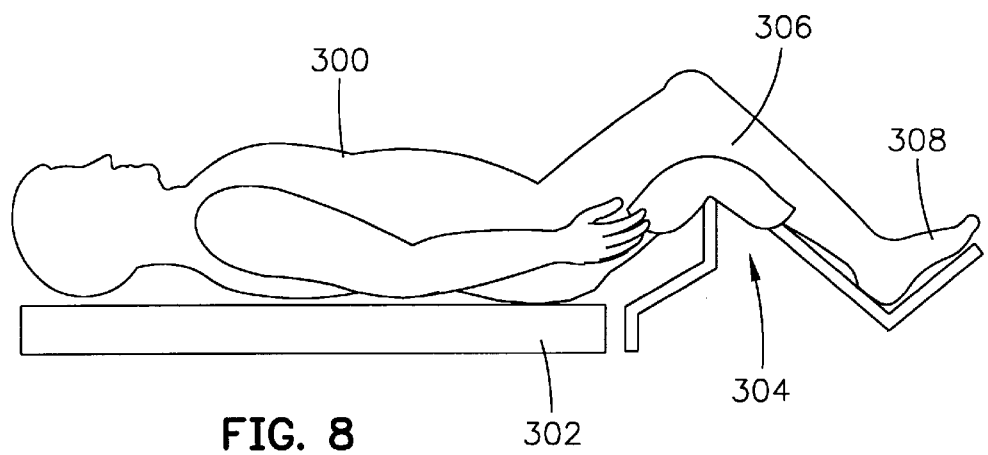
FIG. 8 is a elevational side view showing a patient placed in the lithotomy position.
Figure 9:
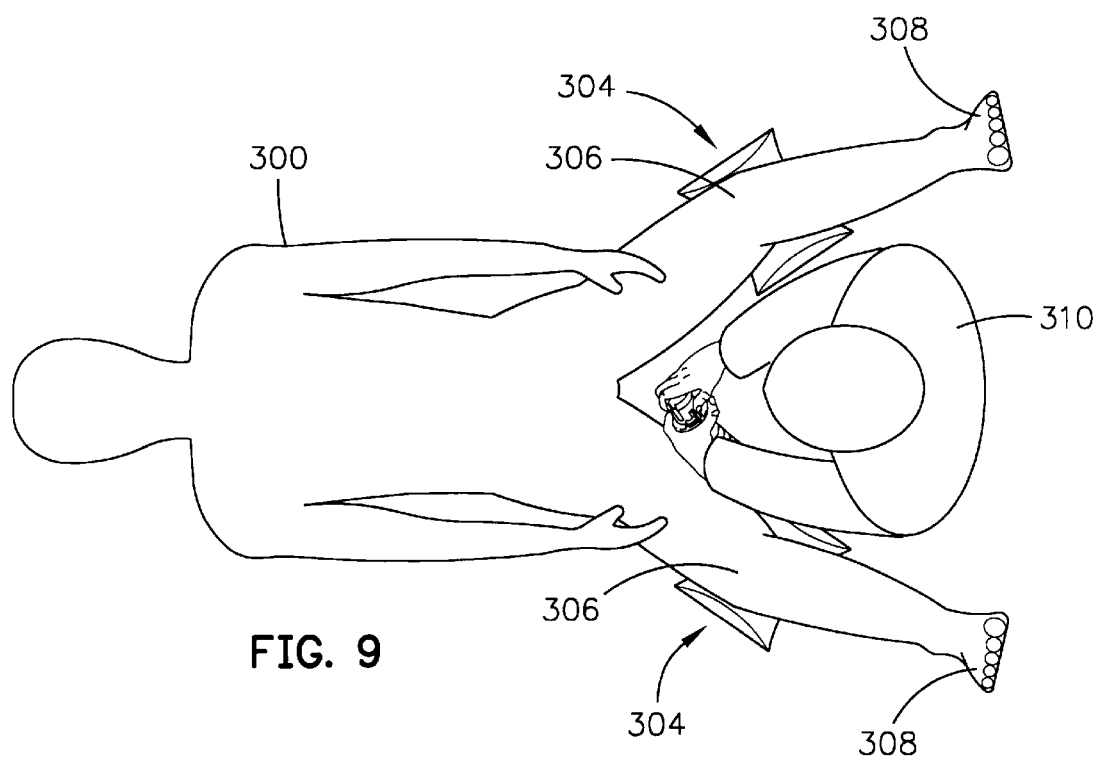
FIG. 9 is a plan view showing a patient placed in the lithotomy position.

Referring now to FIGS. 8–10, an inflatable thermal blanket 320 is constructed to warm convectively by exhausting warm air onto the patient 300. The inflatable thermal blanket 320 may be constructed using materials and constructions discussed in the preceding section; however it is configured for use with patients in the lithotomy position. As in the case of the inflatable thermal blankets disclosed above, the inflatable thermal blanket 320 includes a head end 322, a foot end 324, a pair of outer lateral edges 326 and 327, and an inflation inlet cuff 328 which may be connected through a heater tube, such as the tube 20 shown in FIG. 1, to a heater/blower assembly such as the assembly 18 shown in FIG. 1.

The inflatable thermal blanket further includes a primary inflatable portion 329 configured to cover a patient's torso, and a pair of first and second elongate inflatable portions 330 and 332, respectively, configured to cover a patient's legs. The elongate inflatable portions 330 and 332 are separated to provide an uninflated elongate opening, or cutout, 334 therebetween. The elongate inflatable portions 330 and 332 are defined on their outer sides by portions of the outer lateral edges 326 and 327. The elongate inflatable portions 330 and 332 are defined on their inner sides by a pair of inner lateral edges 336 and 338 that extend from the foot end 324 of the inflatable thermal blanket 320 to a medial transverse edge 340. The inner lateral edges 336 and 338 and the medial transverse edge 340 define the size and shape of the opening 334. The opening 334 has a longitudinal dimension extending from the foot end 324 to the medial transverse edge 340 along a longitudinal axis lying midway between the inner lateral edges 336 and 338. The opening 334 has a transverse dimension, at least at its head end, extending between the inner lateral edges 336 and 338 along a transverse axis lying along the outer edge of the medial transverse edge 340.

The inflatable thermal blanket 320 is formed as an inflatable covering that includes an upper sheet 342 and a base sheet 344, as shown in FIG. 11. These sheets are secured to each other along a peripheral seam 346 that extends beyond the periphery of the inflatable thermal blanket, along the head end 322, the foot end 324, the outer lateral edges 326 and 327, the inner lateral edges 336 and 338, and the medial transverse edge 340. The peripheral seam 346 can be formed by a heat sealing. process as disclosed above. It is preferably continuous, but may also be formed with interruptions along the outer lateral edges 326 and 327 to facilitate egress of the inflating medium, e.g., heated air, as described above. The upper sheet 342 and the base sheet 344 may be constructed using the materials and techniques described above in connection with FIGS. 2–4, or equivalents thereof For example, the upper sheet 342 may comprise a sheet of heat-sealable material, such as plastic, while the base sheet 344 may comprise a lower layer of a flexible, fibrous material laminated to an upper layer of heat-sealable synthetic material, such as plastic, and the thermal blanket 320 may include a parallel array of elongated tubes of which 348 and 350 are the lateral most tubes, 352 is the center tube, and the tubes 354 are arrayed between one of the lateral most tubes and the center tube. Each tube is separated from an adjacent tube by a discontinuous elongated seam formed by an interruptible heat sealing process in the manner disclosed above, one of which is indicated by 356. The seam 356 separates the tube 348 and its nearest adjacent neighbor 354. The discontinuous seam 356 is interrupted by passageways 358 communicating between the tubes.

A plurality of apertures identical to the apertures 62 shown in FIG. 5 open through the base sheet 344 into the inflatable covering. The apertures 62 convectively deliver the inflating medium into the interior space surrounding the patient which is enclosed by the upper and base sheets of the blanket 320.

A pair of uninflatable drapes 360 and 362 help retain the inflating medium proximate to the patient's legs, away from the care site. Each uninflatable drape 360 and 362 extends longitudinally from the foot end 324 toward the head end 346 of the inflatable thermal blanket 320, and laterally from an inner lateral edge 336 or 335 to the elongate opening 334.

The uninflatable drape 360 has a first transverse edge 364 at its foot end, a lateral edge 366, and a second transverse edge 368 at its head end which is parallel to and adjacently spaced from the medial transverse edge 340. The uninflatable drape 362 has a first transverse edge 370 at its foot end, a lateral edge 372, and a second transverse edge 374 at its head end which is parallel to and adjacently spaced from the medial transverse edge 340. The aforementioned edges of the drapes 360 and 362 may be formed by heat sealing in the manner described above.

Each uninflatable drape 360, 362 is preferably formed as an extension of either, or both of, the upper and base sheets 342 and 344 of the elongate inflatable portions 330 and 332. Alternatively, these drapes may comprise separate sheets of material that are attached to the inner lateral edges 336 and 338 of the elongate inflatable portions 330 and 332. Other uninflatable drapes may be provided along the periphery of the inflatable thermal blanket where necessary or appropriate. For example, in the embodiments shown in FIGS. 17 and 18, uninflatable drapes are provided at the head end of the illustrated blankets.

To facilitate use of the inflatable thermal blanket 320 for patients in the lithotomy position, pairs of opposing alcoves may be optionally provided on the inflatable elongate portions 330 and 332 and the drapes 360 and 362. These alcoves are preferably formed as V-shaped (i.e., wedge-shaped) notches, oriented perpendicularly to the longitudinal axis of the elongate recess 334. A first alcove pair consists of an outer alcove 376 formed in the outer lateral edge 326, and an inner alcove 378 formed in the lateral edge 366 of the uninflatable drape 360. A second alcove pair consists of an outer alcove 380 formed in the outer lateral edge 327, and an inner alcove 382 formed in the lateral edge 372 of the uninflatable drape 362.

Figure 14:
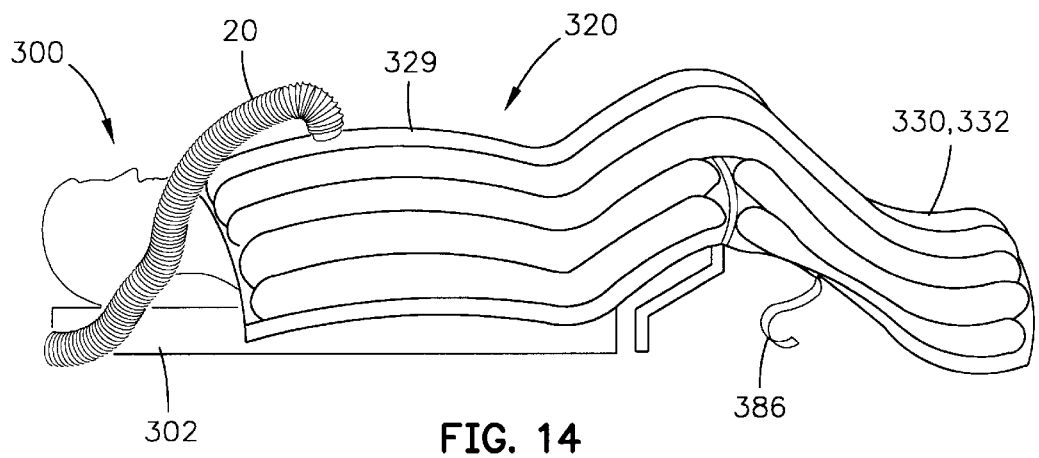
FIG. 14 is a diagrammatic side view showing the inflatable thermal blanket of FIG. 10 superimposed over a patient in the lithotomy position of FIG. 12 to illustrate the relative positions of the blanket and the patient.
Figure 16:
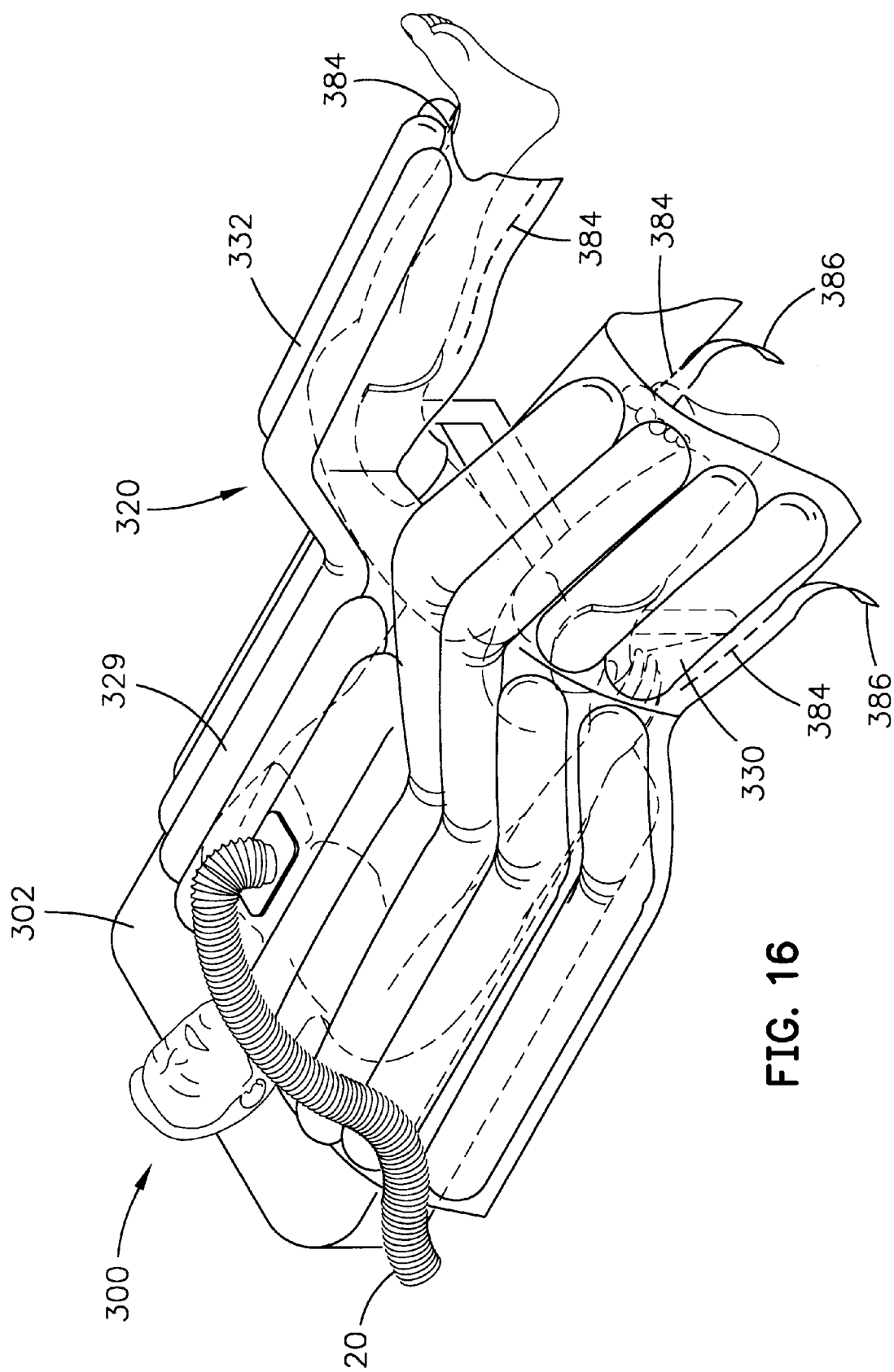
FIG. 16 is a perspective view showing the inflatable thermal blanket of FIG. 10 superimposed over a patient in the lithotomy position to illustrate the relative positions of the blanket and the patient.

In order to assist in retaining the inflatable thermal blanket 320 in position on a patient, the lateral edges 326, 327, 366 and 372 may be provided with perforations 384 which allow portions of the lateral edges to be torn away to form attachment devices, consisting of the strips 386 shown in FIGS. 14 and 16, which can be secured, i.e., tied, to a patient's legs during a surgical procedure.

Figure 15:
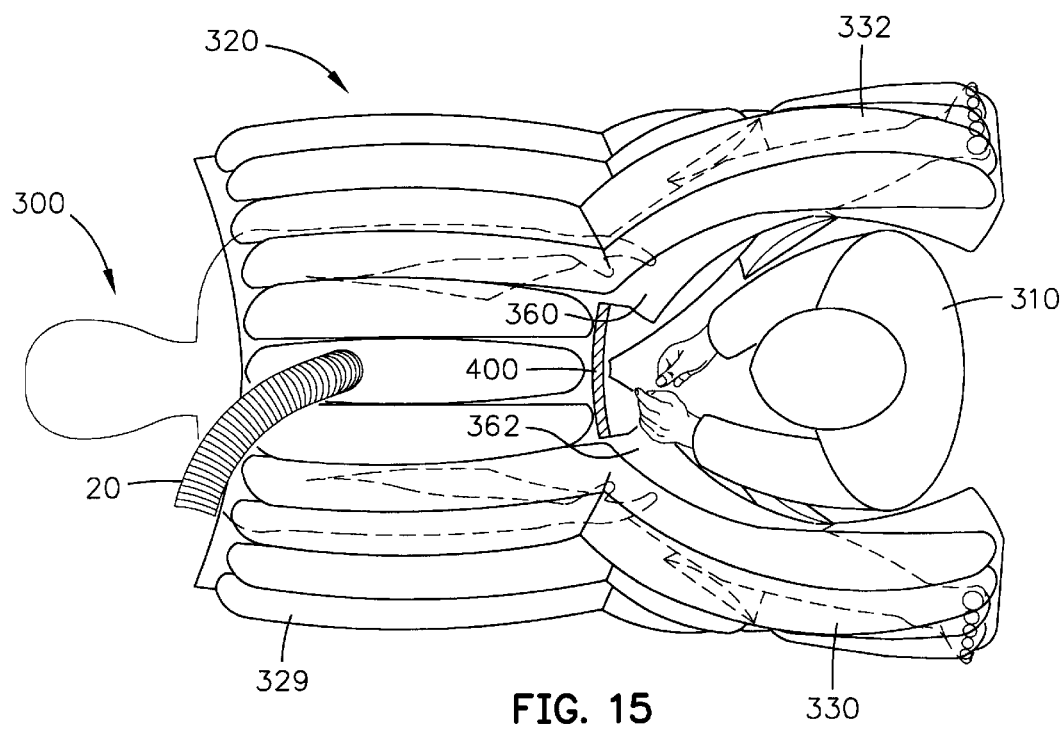
FIG. 15 is a diagrammatic plan view showing the inflatable thermal blanket of FIG. 12 superimposed over a patient in the lithotomy position of FIG. 13 to illustrate the relative positions of the blanket and the patient.

As further shown in FIGS. 14–16, the inflatable thermal blanket 320 is inflated during use to fill the elongated tubes with the inflating medium. This causes the primary inflatable portion 329 to inflate over the patient's torso and the elongate inflatable portions 330 and 332 to inflate over the patient's legs. The uninflatable drapes 360 and 362 advantageously hang downwardly along the inner sides of the patient's legs to help retain the inflating medium near the patient and away from the procedure site. The strips 386 help attach the drapes 360 and 362 to the patient's legs to further retain the inflating medium near the patient.

Figure 12:
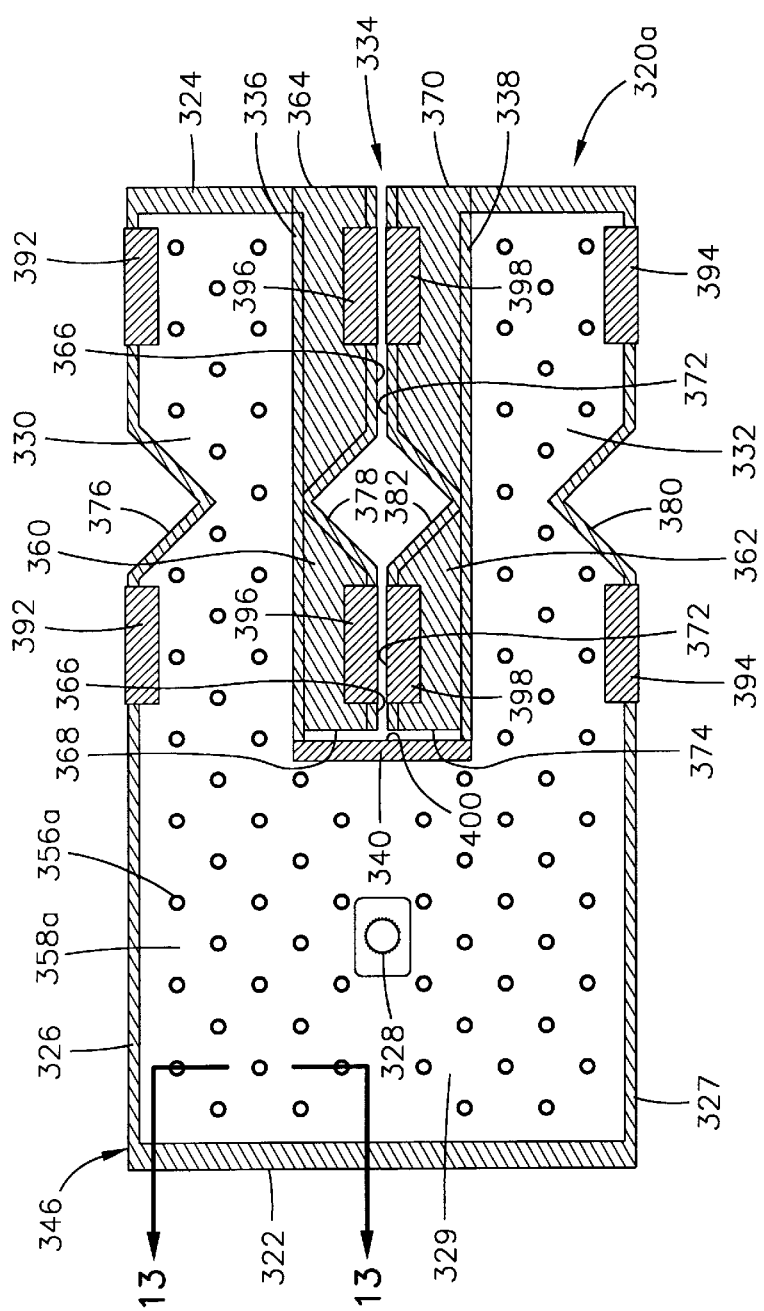
FIG. 12 is a plan view of an inflatable thermal blanket representing an alternative construction to the inflatable thermal blanket of FIG. 10, with the blanket laying flat before being inflated or placed on a patient.
Figure 13:
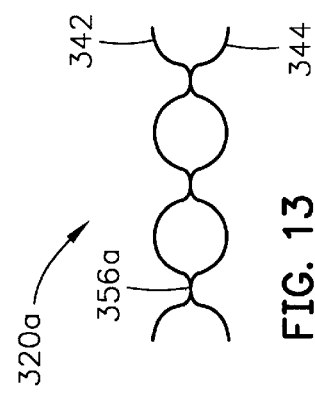
FIG. 13 is a cross sectional view taken along line B—B in FIG. 12.

FIGS. 12 and 13 show alternative constructions in accordance with the present invention in which an inflatable thermal blanket 320a is similar in most respects to the inflatable thermal blanket 320 of FIG. 10, and wherein like elements are designated by like reference numbers. One differentiating feature of the inflatable thermal blanket 320a is that, instead of elongated seals, the blanket 320a is formed with a plurality of discrete sealing points, one of which is indicated by 356a. The sealing points are preferably formed using an interruptible heat sealing process as described above. The discrete sealing points 356a form communicating passageways 358a.

The inflatable thermal blanket 320a further includes attachment devices, consisting of adhesive strips, for securing the elongate inflatable portions 330 and 332 to the patient's legs and for preventing the inflating medium from impinging on the care site. One pair of adhesive strips 392 is mounted on the outer lateral edge 326. A second pair of adhesive strips 394 is mounted on the outer lateral edge 327. A third pair of adhesive strips 396 is mounted on the lateral edge 366. A fourth pair of adhesive strips 398 is mounted on the lateral edge 372. These adhesive strips can be formed in identical fashion to the adhesive strips described above.

To further prevent the inflating medium from impinging on the care site, an attachment device consisting of an adhesive strip 400, can be mounted so as to extend along the medial transverse edge 340. Securing the adhesive strip 400 to the patient blocks the inflating medium a prevents it from escaping past the transverse edge 340. The adhesive strip 400 is shown in use in FIG. 15. It is preferably also used on the inflatable thermal blanket 320 of FIG. 10.

FIGS. 14–16 illustrate how an inflatable thermal blanket constructed in accordance with the present invention covers a patient in the lithotomy position so as to bathe the patient in a temperature control medium while allowing a medical practitioner access to the patient's perineal area. Notice that while the patient is warmed, the medical practitioner can easily access the medical care site. Notice further that the uninflatable drapes 360 and 362, together with the adhesive strip 400, allow the patient to be warmed by air flow coming from the blanket while the care site does not receive any air flow. This is of particular importance because the care site is a sterile area.

Figure 17:
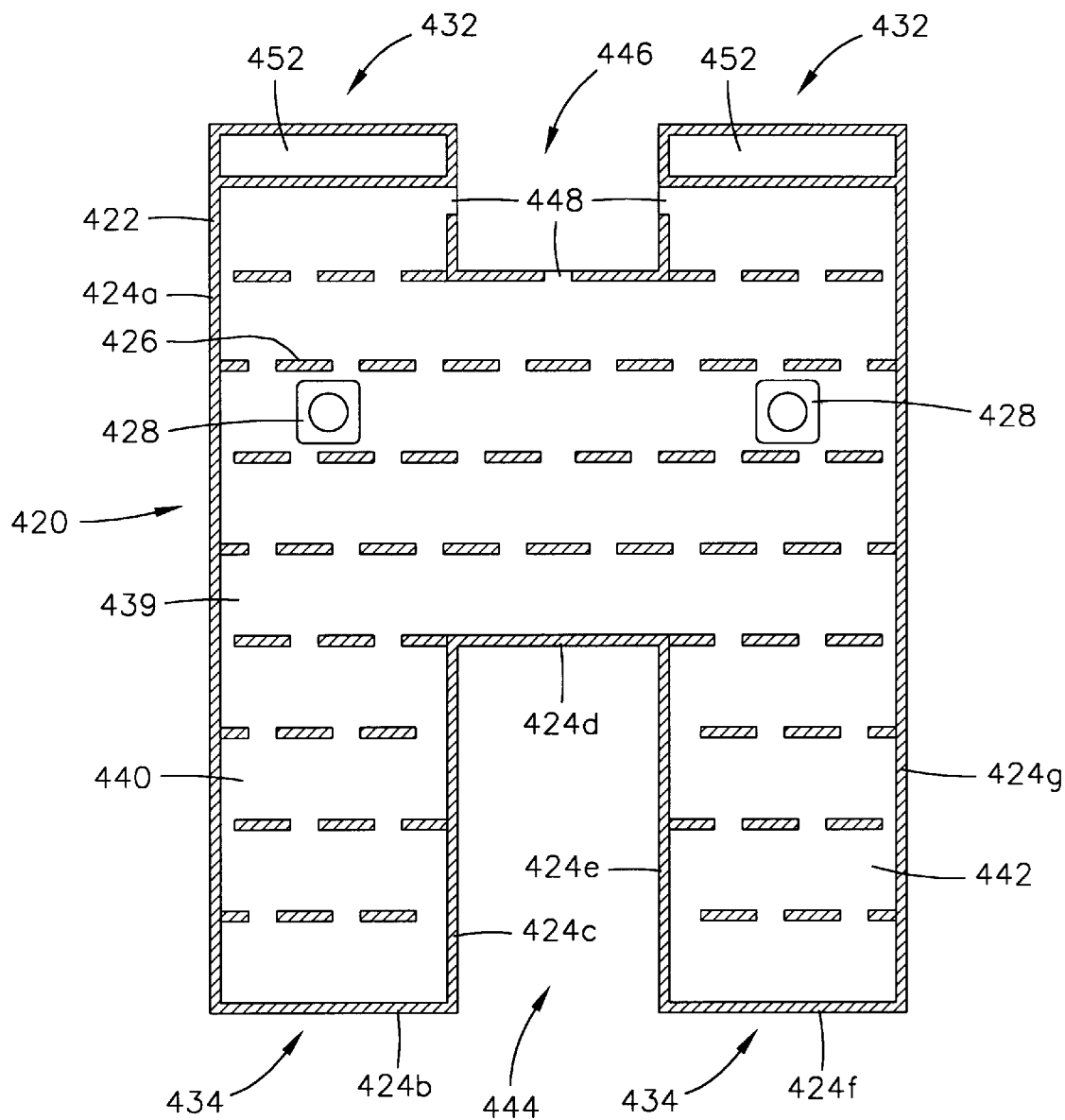
FIG. 17 is a plan view showing an uninflatable thermal blanket representing another alternative construction, with the blanket laying flat before being inflated or placed on a patient.
Figure 19:
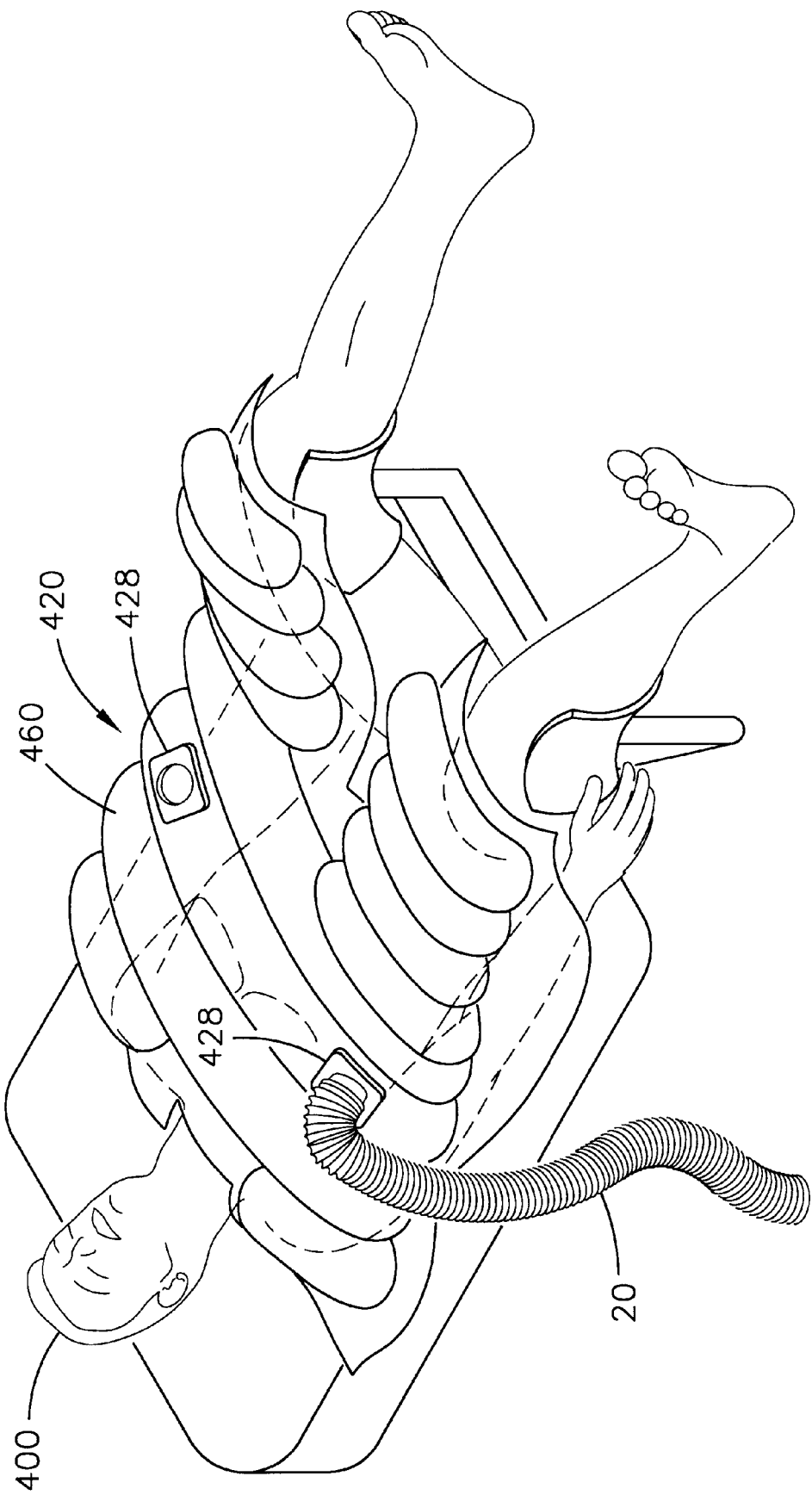
FIG. 19 is a perspective view showing the inflatable thermal blanket of FIG. 17 superimposed over a patient in the lithotomy position to illustrate relative positions of the blanket and the patient.

Referring now to FIGS. 17 and 19, another embodiment of this invention includes an inflatable thermal blanket 420 that is constructed to warm convectively by exhausting warm air onto a patient 400 in the lithotomy position. The inflatable thermal blanket 420 may be constructed using materials and techniques already discussed. However, it is configured with communicating inflatable chambers that extend transversely across the blanket, and across the patient, when inflated and deployed for use. In this regard, inflatable space is provided by joining a base sheet and a top sheet together around a periphery 422 of the blanket 420. For example, near the periphery 422, a continuous seal is formed that comprises sections 424a–424g. The continuous seal near the periphery joins the base sheet to the top sheet as described above. Intermittent seals 426 extend transversely across a longitudinal centerline of the inflatable thermal blanket 420. The base sheet is constructed to exhaust temperature-controlled air from the inflatable thermal blanket 420 when the blanket is inflated. Inflation inlet cuffs 428 are provided laterally of the longitudinal midline of the blanket 420. Either of the inflation inlet cuffs 428 may be used for inflating the blanket, with the unused cuff being sealed or plugged in order to prevent the escape of air. As in the case of the embodiments disclosed above, the inflatable thermal blanket 420 includes a head end 432 and a foot end 434. Further, the inflatable thermal blanket 420 includes a primary inflatable portion 439 configured to cover a patient's torso, and a pair of first and second elongate inflatable portions for 440 and 442, respectively, configured to cover the upper portions of the legs of the patient 400. The elongate inflatable portions 440 and 442 are separated by an opening or cutout 444 therebetween. Also provided is an opening 446 at the head end 432 for accommodating the head of the patient 400. For warning in this space, vents 448 are provided which exhaust warmed air from the inflatable thermal blanket 420 between the edges of the base and upper sheets from which the blanket is formed. Preferably, the vents 448 are formed by discontinuities in the seal near the periphery of the inflatable thermal blanket 420. A pair of uninflatable drapes 452 are formed as described above at the head end 432 of the inflatable thermal blanket 420. The drapes are intended to hang over the shoulders of the patient, trapping warmed air underneath the inflatable thermal blanket 420 at the head end 432. As best seen in FIG. 19, when the nozzle of the air hose 20 is received in one of the inflating inlet cuffs 429 (with the other, unused cuff being plugged or otherwise sealed to prevent the exit of warmed air) the inflatable thermal blanket 420 inflates, displaying a pattern of parallel tubes, one of which is indicated by reference 460, that extend transversely across the body of the patient 400.

Figure 18:
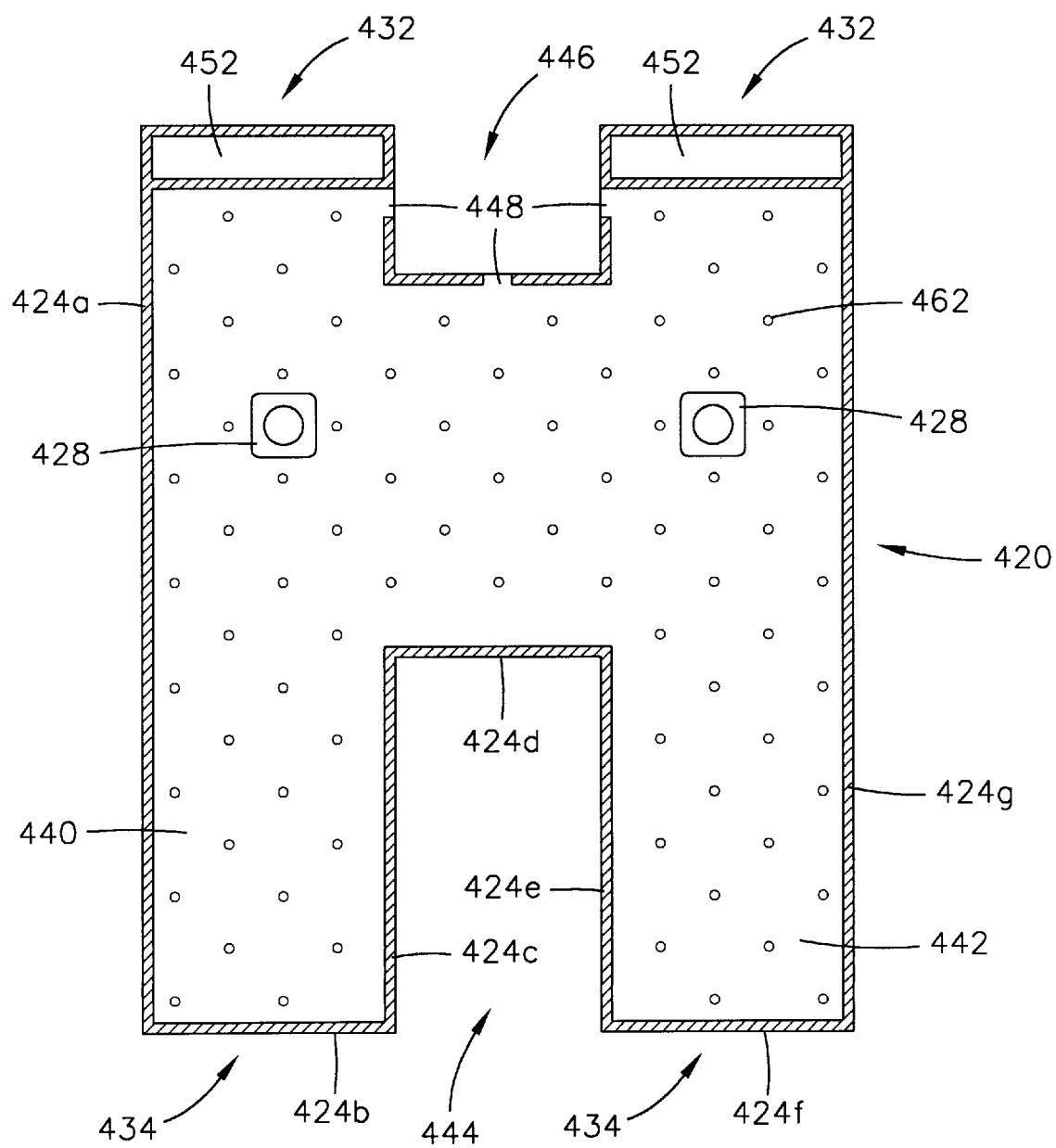
FIG. 18 is a plan view showing an uninflatable thermal blanket representing yet another alternative construction with the blanket laying flat before being inflatable or placed on a patient.

An alternate method of forming the inflatable space in the inflatable thermal 420 is illustrated in FIG. 18 where, within the peripheral seam, the base sheet and top sheet are joined by a pattern of stake points or point seals, one of which is indicated by 462.

Both of the embodiments illustrated in FIGS. 17 and 18 may include uninflatable drapes at their peripheries, where necessary. For example, uninflatable drapes may be provided at the inside edges of the elongate inflatable sections which cover the upper legs of a patient. Adhesive strips and ties may also be provided in these embodiments for attachment to a patient.

Design considerations and clinical requirements should determine the specific configuration of the inflatable thermal blanket of this invention, which is intended for use with patients in the lithotomy position. In this regard, an inflatable thermal blanket with surgical access for use with patients in the lithotomy position may include two elongate portions that are adapted to extend along a patient's legs with any opening between them to provide access to the patient's perineal and groin regions. These sections may be adapted to cover a patient's legs to any point between the ankles and from the knees. Uninflatable drapes my be placed on the inside and outside edges of these sections; uninflatable drapes may also be placed at the head end of the thermal blanket and along the outside edges of the main inflatable portion. When inflated, the inflatable thermal blanket of the invention may exhibit a structure comprising a plurality of parallel tubes that extend longitudinally or transversely. Such tubes are formed by elongate intermittent seals between base and top sheets. Alternatively, the base and top sheets may be staked together using a plurality of point seals within a continuous peripheral seal.

Many modifications and variations of this invention will be evident to those skilled in the art. For example, thermal coverings for additional selected patient areas could be deployed depending on the location of the care site and the need for thermally maintaining other areas. It is understood that such variations may deviate from specific teachings of this description without departing from the essence of the invention, which is expressed in the following claims.

I claim:

1. An inflatable cover for use with a patient in the lithotomy position, comprising:
an inflatable covering with an upper sheet and an air-permeable base sheet;
one or more air inlets in the inflatable covering;
the inflatable covering including a periphery, a head end, and a foot end;
the inflatable covering including a first elongate inflatable portion and a second elongate inflatable portion, the first and second elongate inflatable portions being substantially parallel and extending from the foot end toward the head end;
the first and second elongate inflatable portions being separated along a longitudinal dimension extending from the foot end toward the head end;

one or more uninflatable drapes extending from the periphery; and tie-down strips formed by lines of weakness in the elongate inflatable portions and the one or more uninflatable drapes.

2. An inflatable cover in accordance with claim 1, wherein the first and second elongate inflatable portions are separated along the longitudinal dimension to provide an opening therebetween.

3. An inflatable cover in accordance with claim 2, wherein the elongate inflatable portions and the one or more uninflatable drapes define alcoves positioned medially between the elongate inflatable portions.

4. An inflatable cover in accordance with claim 3, wherein the alcoves are wedge shaped.

5. An inflatable cover in accordance with claim 1, wherein the one or more uninflatable drapes are at the read end.

6. An inflatable cover in accordance with claim 1, wherein the one or more uninflatable drapes are formed by extensions of one, or both, of the upper and base sheets.

7. An inflatable cover in accordance with claim 1, wherein the one or more uninflatable drapes are on the elongate inflatable portions, and extend along the longitudinal dimension.

8. An inflatable cover in accordance with claim 1, wherein the opening further includes a transverse dimension.

9. An inflatable cover in accordance with claim 1, further including an attachment device located near an end of the opening.

10. An inflatable cover in accordance with claim 9, wherein the attachment device comprises an adhesive strip.

11. An inflatable cover in accordance with claim 1, wherein the upper and base sheets are joined together at multiple locations within the periphery.

12. An inflatable cover in accordance with claim 11, wherein the upper and base sheets are joined together by discontinuous seals at the multiple locations.

13. An inflatable cover in accordance with claim 12, wherein the discontinuous seals form a plurality of elongate, substantially parallel chambers.

14. An inflatable cover in accordance with claim 13, wherein the chambers are disposed longitudinally in the inflatable covering.

15. An inflatable cover in accordance with claim 13, wherein the chambers are disposed transversely in the inflatable covering.

16. An inflatable cover in accordance with claim 11, wherein the upper and base sheets are joined together by point seals of the multiple locations.

17. An inflatable cover in accordance with claim 1, further including:

a source of a stream of warmed air for inflating the cover; and an air hose for connecting the source to an air inlet.

18. An inflatable cover for warming a patient in the lithotomy position, comprising;

an inflatable covering with upper and base sheets, the base sheet being air-permeable;

one or more air inlets in the inflatable covering;

the inflatable covering including a periphery, a first end and a second end;

an elongate opening extending from the second end toward the first end;

the elongate opening defining two elongate, substantially parallel inflatable portions in the inflatable covering, each elongate inflatable portion adapted to be disposed adjacent a respective leg of the patient;

the elongate opening adapted to extend between the patient's legs to a portion of the patient near the intersection of the patient's legs;

uninflatable drapes at the periphery; and tie-down strips formed by perforations in the elongate inflatable portions and the uninflatable drapes.

19. An inflatable cover in accordance with claim 18, wherein the uninflatable drapes are formed by extensions of one or both of the upper and base sheets.

20. An inflatable cover in accordance with claim 18 wherein the uninflatable drapes are at the head end.

21. An inflatable cover in accordance with claim 18, wherein the uninflatable drapes are mounted on the elongate inflatable portions and extend into the opening.

22. An inflatable cover in accordance with claim 21, wherein the elongate inflatable portions and the uninflatable drapes define alcoves positioned medially between the elongate inflatable portions.

23. An inflatable cover in accordance with claim 22, wherein the alcoves are wedge shaped.

24. An inflatable cover in accordance with claim 21, wherein the opening further includes a first end and a transverse dimension at the first end.

25. An inflatable cover in accordance with claim 24, wherein the attachment device is located near the first end.

26. An inflatable cover in accordance with claim 18, further including:

a source of a flow of warmed air for inflating the cover; and an air hose for connecting the source to the air inlet.

27. An inflatable cover for use with a patient in the lithotomy position, comprising:

an inflatable covering with an upper sheet and an air-permeable base sheet;

one or more air inlets in the inflatable covering;

the inflatable covering including a periphery, a head end, and a foot end;

the inflatable covering including a first elongate inflatable portion and a second elongate inflatable portion, the first and second elongate inflatable portions being substantially parallel and extending from the foot end toward the head end;

the first and second elongate inflatable portions being separated along a longitudinal dimension extending from the foot end toward the head end;

one or more uninflatable drapes extending from the periphery on the elongate inflatable portions, extending along the longitudinal dimension; and attachment devices, comprised of tie-down strips formed by lines of weakness in the elongate inflatable portions and the one or more uninflatable drapes, for attaching the elongate inflatable portions and the one or more uninflatable drapes to a patient.

28. An inflatable cover for warming a patient in the lithotomy position, comprising;

an inflatable covering with upper and base sheets, the base sheet being air-permeable;

one or more air inlets in the inflatable covering;

the inflatable covering including a periphery, a first end and a second end;

an elongate opening extending from the second end toward the first end;

the elongate opening defining two elongate, substantially parallel inflatable portions in the inflatable covering, each elongate inflatable portion adapted to be disposed adjacent a respective leg of the patient;

the elongate opening adapted to extend between the patient's legs to a portion of the patient near the intersection of the patient's legs;

the opening further includes a first end and a transverse dimension at the first end;

uninflatable drapes at the periphery, mounted on the elongate inflatable portions and extend into the opening;

an attachment device, comprising an adhesive strip, located near the first end; and attachment devices, comprising tie-down strips formed by perforations in the elongate inflatable portions and the uninflatable drapes, for attaching the elongate inflatable portions and the uninflatable drapes to a patient.

* * * * *